(12) United States Patent
Kansal et al.

(10) Patent No.: US 7,687,622 B2
(45) Date of Patent: Mar. 30, 2010

(54) PROCESS FOR PREPARING QUETIAPINE FUMARATE

(75) Inventors: Vinod Kumar Kansal, Haryana (IN); Kanhaiya Lal, Haryana (IN); Suhail Ahmad, New Delhi (IN); David Leonov, Rehovot (IL)

(73) Assignee: Teva Pharmaceutical Industries, Ltd, Petah Tiqva (IL)

( * ) Notice: Subject to any disclaimer, the term of this patent is extended or adjusted under 35 U.S.C. 154(b) by 954 days.

(21) Appl. No.: 11/404,285

(22) Filed: Apr. 14, 2006

(65) Prior Publication Data

US 2006/0276641 A1    Dec. 7, 2006

Related U.S. Application Data

(60) Provisional application No. 60/672,175, filed on Apr. 14, 2005, provisional application No. 60/677,091, filed on May 2, 2005, provisional application No. 60/680,140, filed on May 11, 2005.

(51) Int. Cl.
C07D 281/02 (2006.01)

(52) U.S. Cl. .................................................. 540/551

(58) Field of Classification Search ................. 540/551
See application file for complete search history.

(56) References Cited

U.S. PATENT DOCUMENTS

| | | | |
|---|---|---|---|
| 3,188,323 | A | 6/1965 | Sowinski et al. |
| 4,115,292 | A | 9/1978 | Richardson et al. |
| 4,879,288 | A | 11/1989 | Warawa et al. |
| 4,929,380 | A | 5/1990 | Schultz et al. |
| 6,333,198 | B1 | 12/2001 | Edmeades et al. |
| 6,372,734 | B1 | 4/2002 | Snape |
| 6,534,091 | B1 | 3/2003 | Garces Garces et al. |
| 6,733,790 | B1 | 5/2004 | Garces Garces |
| 6,794,467 | B2 | 9/2004 | Lele et al. |
| 6,818,296 | B1 | 11/2004 | Garces Garces et al. |
| 7,045,621 | B1 | 5/2006 | Harada et al. |
| 7,071,331 | B2 | 7/2006 | Diller et al. |
| 7,238,686 | B2 | 7/2007 | Parthasaradhi et al. |
| 7,314,930 | B2 | 1/2008 | Harada et al. |
| 2002/0147186 | A1 | 10/2002 | Snape |
| 2003/0064106 | A1 | 4/2003 | Garces et al. |
| 2003/0216376 | A1 | 11/2003 | Lifshitz-Liron et al. |
| 2004/0220400 | A1 | 11/2004 | Diller et al. |
| 2004/0242562 | A1 | 12/2004 | Parthasaradhi et al. |
| 2005/0026900 | A1 | 2/2005 | Goldstein |
| 2005/0080072 | A1 | 4/2005 | Deshpande et al. |
| 2005/0192268 | A1 | 9/2005 | Ek et al. |
| 2006/0063927 | A1 | 3/2006 | Etlin et al. |
| 2006/0173178 | A1 | 8/2006 | Harada et al. |
| 2006/0189594 | A1 | 8/2006 | Puig et al. |
| 2006/0223994 | A1 | 10/2006 | Rao et al. |
| 2006/0276641 | A1 | 12/2006 | Kansal et al. |
| 2007/0111986 | A1 | 5/2007 | Hilden et al. |
| 2007/0203336 | A1 | 8/2007 | Murray et al. |

| | | | |
|---|---|---|---|
| 2007/0225494 | A1 | 9/2007 | Kwak et al. |
| 2007/0293471 | A1 | 12/2007 | Kumar et al. |

FOREIGN PATENT DOCUMENTS

| | | |
|---|---|---|
| CN | 101190902 | 6/2008 |
| CN | 101293879 | 10/2008 |
| EP | 0 240 228 A | 10/1987 |
| EP | 0 282 236 A | 9/1988 |
| EP | 1 602 650 A1 | 12/2005 |
| WO | WO 99/06381 A | 2/1999 |
| WO | WO 01/55125 A | 8/2001 |
| WO | WO 02/057402 A1 | 7/2002 |
| WO | WO 03/080065 A | 10/2003 |
| WO | WO 2004/047722 A2 | 6/2004 |
| WO | WO 2004/047722 A3 | 6/2004 |
| WO | WO 2004/076431 | 9/2004 |
| WO | WO 2004/078735 | 9/2004 |
| WO | WO 2004/076431 A1 | 10/2004 |
| WO | WO 2005/012274 A1 | 2/2005 |
| WO | WO 2005/014590 A2 | 2/2005 |
| WO | WO 2005/028457 | 3/2005 |
| WO | WO 2005/028458 | 3/2005 |
| WO | WO 2005/028459 | 3/2005 |
| WO | WO 2006/001619 A1 | 1/2006 |
| WO | WO 2006/027789 A1 | 3/2006 |
| WO | WO 2006/035293 A1 | 4/2006 |
| WO | WO 2006/056771 A1 | 6/2006 |
| WO | WO 2006/056772 A2 | 6/2006 |
| WO | WO 2006/077602 A1 | 7/2006 |
| WO | WO 2006/094549 A1 | 9/2006 |
| WO | WO 2006/113425 A1 | 10/2006 |
| WO | WO 2006/117700 A2 | 11/2006 |
| WO | WO 2006/117700 A3 | 11/2006 |
| WO | WO 2006/135544 A1 | 12/2006 |

(Continued)

OTHER PUBLICATIONS

Haleblian, "Characterization of Habits and Crystalline Modification of Solids and Their Pharmaceutical Applications," Journal of Pharmaceutical Sciences, vol. 64, No. 8, 1975, pp. 1269-1288.
Haleblian, et al., "Pharmaceutical Applications of Polymorphism," Journal of Pharmaceutical Sciences, 1969, pp. 911-929, vol. 58, No. 8.
Merck Index, 13th Ed., 2001, 8127, pp. 1439.
Wall, "Pharmaceutical Applications of Drug Crystal Studies," Pharmaceutical Manufacturing, 1986, pp. 33- 42, vol. 3, No. 2.
Warawa, et al., "Behavioral Approach To Nondyskinetic Dopamine Antagonists: Identification of Seroquel", Journal Of Medicinal Chemistry, American Chemical Society, 2001, pp. 372-389.
J. Schmutz et al. Helv. Chim. Acta, 48: 336 (1965).
Snyder p. 549 (Snyder, L.R. Kirkland, J.J. Introduction to modern liquid chromatography, 2nd ed. (John Wiley & Sons: NY 1979).

Primary Examiner—Brenda L Coleman
(74) Attorney, Agent, or Firm—Kenyon & Kenyon LLP

(57) ABSTRACT

Provided is a novel synthesis of quetiapine, and pharmaceutically acceptable salts thereof, in which an alkali metal halide or siliyl halide is included in the reaction mixture.

29 Claims, No Drawings

FOREIGN PATENT DOCUMENTS

| | | |
|---|---|---|
| WO | WO 2007/004234 A1 | 1/2007 |
| WO | WO 2007/020011 A1 | 2/2007 |
| WO | WO 2007/036599 A1 | 4/2007 |
| WO | WO 2007/048870 A1 | 5/2007 |
| WO | WO 2007/062337 A2 | 5/2007 |
| WO | WO 2007/102074 A2 | 9/2007 |
| WO | WO 2007/102352 A2 | 9/2007 |
| WO | WO 2008/003270 A1 | 1/2008 |

PROCESS FOR PREPARING QUETIAPINE FUMARATE

RELATED APPLICATIONS

The present application claims the benefit of the Apr. 14, 2005 filing date of the U.S. Provisional Patent Application 60/672,175, the May 2, 2005 filing date of the U.S. Provisional Patent Application 60/677,091 and the May 11, 2005 filing date of the U.S. Provisional Patent Application 60/680,140.

FIELD OF THE INVENTION

The present invention relates to synthesis of quetiapine and pharmaceutically acceptable salts thereof.

BACKGROUND OF THE INVENTION

Quetiapine,2-(2-(4-dibenzo[b,f][1,4]thiazepin-11-yl-1-piperazinyl)ethoxy)ethanol, having the following chemical structure:

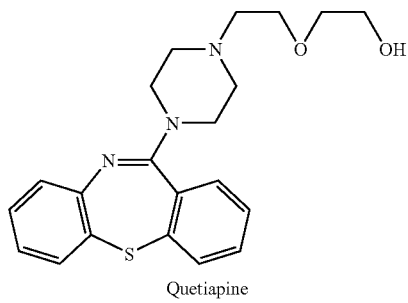

Quetiapine is a psychoactive organic compound that acts as an antagonist for multiple neurotransmitter receptors in the brain and acts as an antipsychotic agent reportedly useful for treating, among other things, schizophrenia. *Merck Index,* 13th Ed., 8130 (2001). This drug, having the CAS number: 111974-69-7, was approved under the trademark Seroquel®, by the U.S. Food and Drug Administration and is available from the innovator, AstraZeneca PLC. Quetiapine can be made, for example, as taught in the U.S. Pat. No. 4,879,288, incorporated in its entirety herein by reference.

As taught in the '288 patent, quetiapine can be made via reaction of formula I, 11-piperazinyl dibenzo[b,f]-[1,4]thiazepine hydrochloride and about a 2 molar equivalent of formula II, 1-(2-hydroxyethoxyethyl)piperazine,

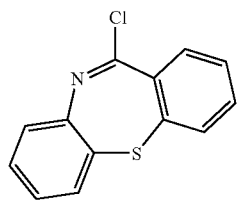

I

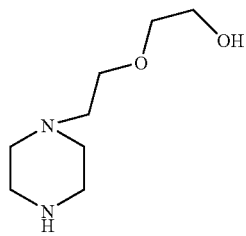

II wherein the reaction time is about 30 hours, the yield is about 77%, and puritfication is by flash chromotpgraphy.

Thus, there is a need in the art for an improved process for making quetiapine and salts thereof from 11-piperazinyl dibenzo[b,f]-[1,4]thiazepine and 2-(2-chloroethoxy)ethanol using less than a 2 molar equivalent of 2-(2-chloroethoxy)ethanol with respect to 11-piperazinyl dibenzo[b,f]-[1,4]thiazepine, a shorter reaction time, and affording a quetiapine product that contains a lower level of impurities (such as the unreacted starting material) so that the process can be easily, conveniently, and inexpensively applied on an industrial scale.

SUMMARY OF THE INVENTION

In one embodiment, the present invention provides a method of preparing quetiapine comprising: reacting 11-chlorodibenzo[b,f][1,4]-thiazepine with 1-(2-hydroxyethoxyethyl)piperazine in a reaction solvent selected from the group consisting of: $C_5$ to $C_{12}$ saturated or aromatic hydrocarbons, $C_1$ to $C_4$ alcohols, $C_1$ to $C_4$ alkyl esters, $C_2$ to $C_8$ ketones, $C_2$ to $C_8$ linear, branched or cyclic or acyclic ethers, $C_3$ to $C_{10}$ alkyl esters, and $C_1$ to $C_4$ alkyl nitriles, or mixtures thereof, in the presence of at least one organic or inorganic base, and an alkali metal halide or a silyl halide to obtain quetiapine; and recovering the obtained quetiapine.

In another aspect, the present invention relates to a method of preparing a pharmaceutically acceptable salt of quetiapine comprising combining an acid with the quetiapine prepared according to the process described above; and recovering the obtained pharmaceutically acceptable salt of quetiapine. Preferably, the pharmaceutically acceptable salt is quetiapine fumarate, and the acid is fumaric acid.

In another embodiment, the present invention provides a method for preparing quetiapine comprising: reacting 11-chlorodibenzo[b,f][1,4]-thiazepine with 1-(2-hydroxyethoxyethyl)piperazine in a reaction solvent selected from the group consisting of: $C_5$ to $C_{12}$ saturated or aromatic hydrocarbons, $C_1$ to $C_4$ alcohols, $C_1$ to $C_4$ alkyl esters, $C_2$ to $C_8$ ketones, $C_2$ to $C_8$ linear, branched or cyclic or acyclic ethers, $C_3$ to $C_{10}$ alkyl esters, and $C_1$ to $C_4$ alkyl nitriles, or mixtures thereof, in the presence of at least one organic or inorganic base, and a phase transfer catalyst; and recovering the obtained quetiapine.

In another aspect, the present invention relates to a method of preparing a pharmaceutically acceptable salt of quetiapine comprising combining an acid with the quetiapine prepared according to the process described above; and recovering the obtained pharmaceutically acceptable salt of quetiapine.

Preferably, the pharmaceutically acceptable salt is quetiapine fumarate, and the acid is fumaric acid.

DETAILED DESCRIPTION OF THE INVENTION

In one embodiment, the present invention provides a method of preparing quetiapine including the steps of: reacting 11-chlorodibenzo[b,f][1,4]-thiazepine, herein "I" with 1-(2-hydroxyethoxyethyl)piperazine, herein "II", in a reaction solvent selected from the group consisting of: $C_5$ to $C_{12}$ saturated or $C_6$ to $C_{12}$ aromatic hydrocarbons, $C_1$ to $C_4$ alcohols, $C_1$ to $C_4$ alkyl esters, $C_2$ to $C_8$ ketones, $C_2$ to $C_8$ linear, branched or cyclic or acyclic ethers, $C_3$ to $C_{10}$ alkyl esters, and $C_1$ to $C_4$ alkyl nitriles, or mixtures thereof, in the presence of at least one organic or inorganic base, and, particularly, a halide compound that is an alkali metal halide or a silyl halide to obtain quetiapine; and, optionally, recovering the obtained quetiapine.

Alkali metal halides useful in the practice on the present invention include alkali metal fluorides, iodides, or bromides. Alkali metal iodides are preferred. Silylhalides can also be used in the practice of the method of the present invention. Potassium iodide (KI) is a particularly preferred alkali metal halide for use in the practice of the present invention. The alkali metal or silylhalide is used in a molar ratio of about 0.2 or greater relative to the moles of I used.

In another embodiment, the present invention provides a method for preparing quetiapine comprising: reacting 11-chlorodibenzo[b,f][1,4]-thiazepine with 1-(2hydroxyethoxyethyl)piperazine in a reaction solvent selected from the group consisting of: $C_5$ to $C_{12}$ saturated or aromatic hydrocarbons, $C_1$ to $C_4$ alcohols, $C_1$ to $C_4$ alkyl esters, $C_2$ to $C_8$ ketones, $C_2$ to $C_8$ linear, branched or cyclic or acyclic ethers, and $C_1$ to $C_4$ alkyl nitriles, or mixtures thereof, in the presence of at least one organic or inorganic base, and a phase transfer catalyst; and, optionally, recovering the obtained quetiapine.

Suitable phase transfer catalysts are ammonium salts such as tricaprylylmethylammonium chloride (Aliquat® 336), tetra-n-butylammonium bromide ("TBAB"), benzyltriethylammonium chloride ("TEBA"), cetyltrimethylammonium bromide, cetylpyridinium bromide, N-benzylquininium chloride, tetra-n-butylammonium chloride, tetra-n-butylammonium hydroxide, tetra-n-butylammonium iodide, tetraethylammonium chloride, benzyltributylammonium bromide, benzyltriethylammonium bromide, hexadecyltriethylanmuonium chloride, tetramethylammonium chloride, hexadecyltrimethyl ammonium chloride, and octyltrimethylammonium chloride. More preferred phase transfer catalysts are Aliquat.RTM 336, TBAB, TEBA and mixtures thereof, the most preferred being Aliquat.RTM 336 Inorganic bases useful in the practice of the present invention include alkali metal carbonates or hydroxides, for example potassium bi/carbonate, sodium bi/carbonate, or sodium hydroxide, cesium carbonate/hydroxide. Metal carbonate is a preferred inorganic base for use in the practice of the present invention.

When quetiapine is to be isolated, the reaction mixture is cooled to a convenient working temperature, for example room temperature, and combined with aqueous non-oxidizing acid (e.g. HCl). The layers are separated and the aqueous phase optionally washed and the organic layers combined. The combined organic layers are concentrated to afford quetiapine. The quetipine can be recrystallized from a suitable solvent, for example ethyl acetate.

In the processes described above, the reaction temperature is about room temperature (typically 22° to 27° C.) to about reflux temperature, preferably at about reflux temperature.

Preferably, the reaction solvent is a halogenated hydrocarbon or alkyl ester. Toluene and xylenes are particularly preferred reaction solvents, but alkyl alcohols (e.g. n-butanol) are also very suitable as reaction solvents in the practice of the present invention.

Preferably, the 11-chlorodibenzo[b,f][1,4]thiazepine (I) is in the amount of about 1 to about 1.5, preferably about 1 to about 1.2, molar equivalents (based on the moles of I) of 1-(2-hydroxyethoxy)ethyl piperazine (II).

Inorganic bases useful in the practice of the present invention are well known to the skilled artisan and include alkali metal carbonates, alkali metal bicarbonates, and alkali metal hydroxides. Organic bases usefull in the practice of the present invention include mono-, di- or tri-($C_1$ to $C_4$ alkyl) amines such as N,N-dimethylanaline and N,N-diisopropyl ethyl amine. Tertiary amines are preferred organic bases for use in the practice of the present invention. The organic or inorganic base is preferably used in a molar amount between about 1 and about 3, more preferably about 2, times the molar amount of I used in the reaction.

Preferably, the resulting crude quetiapine in the processes described above can then be isolated. Isolation is preferably by cooling the reaction mixture to a convenient temperature, for example room temperature. The optionally cooled reaction mixture is then treated with a nonoxidizing inorganic acid, preferably a mineral acid, for example hydrochloric acid. The inorganic acid can be and preferably is used as its aqueous solution. When an aqueous solution of a nonoxidizing acid is used, a two-phase mixture is obtained if preferred reaction solvents are used. The phases, when present, are separated and the aqueous phase is basified with an inorganic base such as a metal hydroxide or carbonate. The basified aqueous phase is extracted with an organic solvent, especially an organic solvent useful as a reaction solvent. The quetiapene base is obtained after removing the organic solvent, for example by distilling-off the solvent. Prior to isolation, the separated aqueous phase can be extracted with a reaction solvent that is the same or different from the solvent used in the first step, and the extract combined with the separated non-aqueous phase, whereafter the product is isolated from the combined reaction mixture and extracts, if any. By this process a purity of more than 90 area % as measured by high pressure liquid chromatography, more preferably more than 95 area % as measured by HPLC and most preferably more than 97 area % as measured by HPLC, without the need for subjecting the crude product to purification by, for example, flash chromatography.

Reaction times of 20 hours or less, preferably about 10 to about 14 hours, are readily achievable in preferred embodiments of the present invention. The skilled artisan will know to monitor and adjust the reaction time by, for example, monitoring the disappearance of the limiting reagent, compound I in preferred embodiments, using a suitable technique, for example thin layer chromatography, gas-liquid chromatography, or high pressure liquid chromatography, to mention just three.

In another aspect, the present invention relates to a method of preparing a pharmaceutically acceptable salt of quetiapine comprising combining an acid with the quetiapine prepared according to the processes described above; and recovering the obtained pharmaceutically acceptable salt of quetiapine. Preferably, the pharmaceutically acceptable salt is quetiapine fumarate, and the acid is fumaric acid.

The general reaction scheme for preparing quetiapine fumarate is as follows:

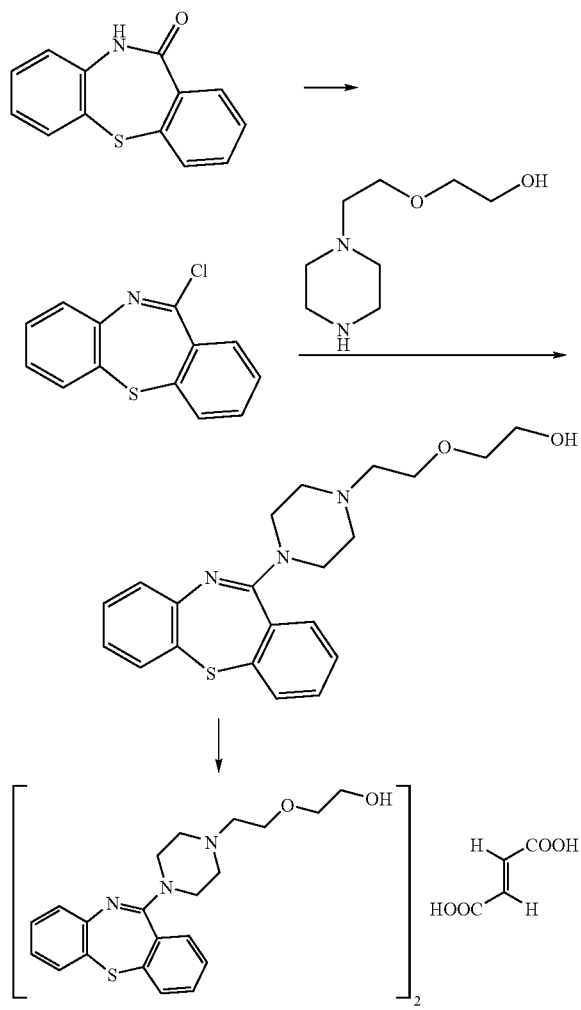

In another embodiment of the present invention, a method is presented of preparing quetiapine and pharmaceutically acceptable salts thereof, preferably the hemi fumarate salt, comprising reacting 11-chlorodibenzo[b,f][1,4]-thiazepine (I) with 1-(2-hydroxyethoxyethyl)piperazine in a reaction solvent selected from the group consisting of: $C_5$ to $C_{12}$ saturated or aromatic hydrocarbon, $C_1$ to $C_4$ alcohol, $C_1$ to $C_4$ alkyl esters, $C_2$ to $C_8$ ketones, $C_2$ to $C_8$ linear, branched or cyclic or acyclic ethers, $C_3$ to $C_{10}$ alkyl esters, and $C_1$ to $C_4$ alkyl nitrile, in the presence of at least one organic or inorganic base, and a phase transfer catalyst. Preferably, the resulting quetiapine can then be isolated by acidification and extraction to obtain a purity of more than 90 area % as measured by HPLC, more preferably more than 95 area % as measured by HPLC and most preferably more than 97 area % as measured by HPLC.

The crude product isolated from the reaction is sufficiently pure, typically ≧97 area-% pure as measured by high pressure liquid chromatography, to be used in subsequent processing, for example conversion to a pharmaceutically acceptable salt, especially the hemifumarate, without the need for subjecting the crude product to purification by, for example, flash chromatography.

Preferably, the quetiapine fumarate is made by a one-pot synthesis, i.e., fumaric acid is combined directly with quetiapine prepared by processes of the invention without first having to isolate the quetiapine.

The present invention in certain of its embodiments is illustrated in the following non-limiting examples. In the examples, "HPLC area-%" refers to purity on an area percent basis as determined from the area under the peaks in the HPLC chromatogram.

Analytical

Quetiapine can be analyzed by the following HPLC method.
1: Acetonitrile (HPLC grade)
2: Water (HPLC grade)
3: Ammonium acetate (AR grade)
4: Ammonia (AR grade)
5: Acetic acid (AR grade)

Preparation of Buffer
Weigh accurately about 3.08 gm (0.04M) ammonium acetate in water add 2.0 ml of 25% ammonium hydroxide per 1000 ml of buffer and mix. pH of the buffer should not be less than 9.2. Change the buffer daily.
Eluent A: Buffer
Eluent B: Acetonitrile Diluent
Acetonitrile.

| Chromatographic conditions | |
|---|---|
| Column | Xterra RP8, 3.5μ, 150 × 4.6 mm, Waters |
| Flow | 1.5 ml/min |
| Injection volume | 20 μl |
| Column temperature | 45° C. |
| Detector | UV at 250 nm |
| Autosampler Temp | 10° C. |

| Gradient Programming: | | |
|---|---|---|
| Time | % Eluent A | % Eluent B |
| 0 | 75 | 25 |
| 25 | 75 | 25 |
| 60 | 22 | 78 |
| 61 | 75 | 25 |
| 70 | 75 | 25 |

Before starting an analysis, wash the column for 30 min with the following eluent: Eluent A20%: Eluent B 80%.

Preparation of System Suitability Solution
Prepare a mixture of about 1.0 mg/ml of Quetiapine fumarate and 0.002 mg/ml of DBTP in diluent.

Evaluation of System Suitability Test
Inject 20 μl of system suitability solution.
A resolution factor between DBTP and Quetiapine peaks of not less than 7.0 should be achieved.
Typical retention times are ~17.5 minutes for DBTP and ~25.0 minutes for Quetiapine.

Preparation of Sample Solution
Prepare about 1 mg/ml solution of Quetiapine Base sample.

Procedure

Inject diluent as a blank.

Inject sample solution into the chromatograph, continuing the chromatogram for whole gradient profile. Determine the area of all peaks using suitable integrator.

Disregard any peak eluting till 2 min and any peak from the diluent.

Disregard any peak less than 0.05%.

Calculation $$\% \text{ Impurity} = \frac{\text{Area of impurity in the sample}}{\text{Sum of area of all peaks in the chromatogram}} \times 100$$

Note:

DBT: Di benzo[b,f][1,4]thiazepine-11(10H)-one.
CDBT: Chloro dibenzo[b,f][1,4]thiazepine-11(10H)-one.
Quetiapine hemifumarate Reagents
1: Acetonitrile (HPLC grade)
2: Ammonium acetate (AR grade)
3: Ammonium hydroxide (AR grade)
4: Acetic acid (AR grade)

Preparation of Buffer

Prepare 0.04 M Ammonium acetate in water and add 2.0 ml of 25% ammonium hydroxide per 1000 ml of buffer solution. pH of the buffer should not be less than 9.2. Change the buffer daily.

Eluent A: Buffer
Eluent B: Acetonitrile (gradient grade)

| Chromatographic conditions | |
|---|---|
| Column: | XTerra RP$_8$, 3.5μ, 150 × 4.6 mm, Waters |
| Flow | 1.5 ml/min |
| Sample Volume | 20 μl |
| Detector | 250 nm |
| Column temperature | 45° C. |

| Gradient Programming | | |
|---|---|---|
| Time | % Eluent A | % Eluent B |
| 0 | 75 | 25 |
| 25 | 75 | 25 |
| 60 | 22 | 78 |

Equilibration time: 8 minutes

Before starting an analysis, wash the column for 30 min with the following eluent: Eluent A 20%: Eluent B 80%. Mobile phase composition and flow rate may be varied in order to achieve the required system suitability.

Preparation of System Suitability Solution

Prepare a mixture of about 1.0 mg/ml of Quetiapine fumarate standard and 0.002 mg/ml of DBTP standard in diluent.

System Suitability Test

Inject system suitability solution.

A resolution factor between DBTP and Quetiapine peaks of not less than 7.0 should be achieved.

Typical retention times are ~17.5 minutes for DBTP and ~25.0 minutes for Quetiapine. Column efficiency for Quetiapine peak of not less than 10000 should be achieved.

Preparation of Sample Solution

Prepare accurately, 1 mg/ml solution of Quetiapine fumarate sample in diluent.

Procedure

Inject the sample solutions into the chromatograph, continuing the chromatogram for whole gradient profile.

Determine the area of all peaks using suitable integrator.

Disregard any peak eluting till 2 min and any peak from the injection of diluent.

Disregard peaks less than 0.02% area

Calculation a.) Calculate contents of QTP-triether, QTP-desethanol and DBTP-ethyl identified by RRT and DBTP identified by SST, according to their relative response factor (F).

$$F = \frac{\text{Response factor of known impurity}}{\text{Response factor of } QTP}$$

$F = 0.62$ for $QTP$-triether $(RRT\ 0.32)$
$F = 1.2$ for $DBTP\ (RRT\ 0.72)$
$F = 1.0$ for $QTP$-desethanol $(RRT\ 0.84)$
$F = 1.1$ for $DBTP$-ethyl $(RRT\ 1.5)$ Known impurities are calculated as following:

$$\% \text{ impurity known} = \frac{\text{Area of impurity}/F \text{ in sample}}{\text{Area of } QYP + \text{Area of other peaks} + \text{known peaks}/F}$$

b.) Calculate any other impurities as follows:

$$\% \text{ impurity } i = \frac{\text{Area of impurity } i \text{ in sample}}{\text{Area of } QYP + \text{Area of other peaks} + \text{known peaks}/F}$$

RL is 0.05%
DL is 0.02%

Abbreviation:
DBTP: Dibenzo[b,f][1,4]thiazepine, 11-(1-piperazine)
QTP: Quetiapine Fumarate
QTP-desethanol: 2-[4-(dibenzo[b,f][1,4]thiapin-11-yl)piperazin-1-yl)]ethanol
QTP-triether: 2-(2-[4-(dibenzo[b,f][1,4]thiapin-11-yl)piperazin-1-yl)]triethoxyethanol
DBTP-ethyl: 4-Ethyl(dibenzo[b,f][1,4]thiapin-11-yl)piperazin-1-yl

EXAMPLES

Example 1

Preparation of 11-[4-[2-(2-Hydroxyethoxy)ethyl]-1-piperazinyl]dibenzo[b,f][1,4]thiazepine A 2 liter round bottom flask equipped with stirring rod, thermo pocket, reflux condenser and nitrogen inlet was charged with 50 gm (0.2 moles) of 11-chlorodibenzo[b,f][1, 4]-thiazepine (I), 500 cc toluene and the mixture was stirred for 15 min. at room temperature. The resulting solution was combined with 39 gm (0.22 mole) of 1-(2-hydroxyethoxy) ethylpiperazine (II), 56.2 gm (0.40 mole) of potassium carbonate and 16.89 gm (0.10 mole) of potassium iodide. The reaction mixture was heated at gentle reflux for 12 hrs and a sample of the reaction mixture was analyzed by HPLC. The analysis revealed that less than 1% of the starting material remained. The reaction mixture was cooled to room temperature and combined with 1000 cc 1N hydrochloric acid solution to get a pH in between 1 to 2. The layers were separated and the aqueous layer was diluted with 500 cc toluene and pH was adjusted between 8 to 9 by addition of sodium carbonate. The layers (aqueous and nonaqueous reaction solvent toluene) were separated and the aqueous layer was extracted with 500 cc toluene. The organic (toluene) layers were combined and washed with 2×500 cc of water. The reaction solvent (toluene) was distilled-off under vacuum at 70 to 80° C. to afford 60 gm oil. HPLC area %: 99.5

Example 2

Preparation of 11-[4-[2-(2-Hydroxyethoxy)ethyl]-1-piperazinyl]dibenzo[b,f][1,4]thiazepine A 2 liter round bottom flask equipped with stirring rod, thermo pocket, reflux condenser and nitrogen inlet was charged with 50 gm (0.2 moles) of 11-chlorodibenzo[b,f][1,4]-thiazepine (I) and 500 cc xylene and the mixture was stirred for 15 min. at room temperature. The resulting solution was combined with 39 gm (0.22 mole) of 1-(2-hydroxyethoxy)ethylpiperazine, 56.2 gm (0.40 mole) of potassium carbonate and 16.89 gm (0.10 mole) of potassium iodide. The reaction mixture was heated at gentle reflux for 12 hrs and a sample of the reaction mixture was analyzed by HPLC. The analysis revealed that less than 1% of starting material I remained. The reaction mixture was cooled to room temperature and treated with 1000 cc 1N hydrochloric acid solution to get a pH in between 1 to 2. The layers were separated and the aqueous layer was agitated with 500 cc xylene and the pH was adjusted between 8 to 9 by addition of sodium carbonate. The layer s were separated and the aqueous layer was extracted with 500 cc xylene. The organic (xylene reaction solvent) layers were combined and washed with 2×500 cc of water. The solvent was distilled-off under vacuum at 70 to 80° C. to afford 60 gm oil. HPLC area %: 99.5

Example 3

Preparation of 1-[4-[2-(2-Hydroxyethoxy)ethyl]-1-piperazinyl]dibenzo[b,f][1,4]thiazepine A 2 liter round bottom flask equipped with stirring rod, thermo pocket, reflux condenser and nitrogen inlet was charged with 50 gm (0.2 moles) of 11-chlorodibenzo[b,f][1,4]-thiazepine and 500 cc n-butanol and the mixture was stirred for 15 min. at room temperature. The resulting solution was combined with 39 gm (0.22 mole) of 1-(2-hydroxyethoxy)ethylpiperazine, 56.2 gm (0.40 mole) of potassium carbonate and 16.89 gm (0.10 mole) of potassium iodide. The reaction mixture was heated at gentle reflux for 12 hrs and a sample of the reaction mixture was analyzed by HPLC. The analysis revealed that starting material remains less than 1%. The reaction mixture was cooled to room temperature and treated with 1000 cc 1N hydrochloric acid solution to get a pH in between 1 to 2. The layers (aqueous and nonaqueous reaction solvent) were separated and the aqueous layer was extracted with 500 cc toluene and pH was adjusted between 8 to 9 by addition of sodium carbonate. The layers were separated and aqueous layer was again extracted with 500 cc toluene. The organic layers (n-butanol and toluene) were combined and washed with 2×500 cc of water. The solvent was distilled under vacuum at 70 to 80° C. to afford 47.5 gm oil. HPLC area %: 98.9

Example 4

Preparation of 11-[4-[2-(2-Hydroxyethoxy)ethyl]-1-piperazinyl]dibenzo[b,f][1,4]thiazepine A 1 liter round bottom flask equipped with stirring rod, thermo pocket, reflux condenser and nitrogen inlet was charged with 10 gm (0.04 moles) of 11-chlorodibenzo[b,f][1,4]-thiazepine, 100 cc toluene and the mixture was stirred for 15 min. at room temperature. The resulting solution was combined with 7.7 gm (0.044 mole) of 1-(2-hydroxyethoxy)ethylpiperazine, 8.5 gm (0.08 mole) of sodium carbonate and 1.6 gm (0.01 mole) of sodium iodide. This reaction mixture was heated at gentle reflux for 15 hrs and the sample was analyzed by HPLC. The analysis revealed that starting material remains less than 1%. The reaction mixture was cooled to room temperature and treated with 175 cc 1N hydrochloric acid solution to get a pH in between 1 to 2. The layers were separated and the aqueous layer was diluted with 100 cc toluene and pH was adjusted to about 8 to 9 using sodium carbonate. The layer s were separated and aqueous layer was extracted with 100 cc toluene. The organic layers were combined and washed with 2×100 cc of water. The solvent was distilled under vacuum at 70 to 80° C. to afford 11 gm oil. HPLC area %: 98.3%

Example 5 (Comparative)

Preparation of 11-[4-[2-(2-Hydroxyethoxy)ethyl]-1-piperazinyl]dibenzo[b,f][1,4]thiazepine A 1 liter round bottom flask equipped with stirring rod, thermo pocket, reflux condenser and nitrogen inlet was charged with 10 gm (0.04 moles) of 11-chlorodibenzo[b,f][1,4]-thiazepine, and 100 cc toluene and the mixture was stirred for 15 min. at room temperature. The resulting solution was combined with 7.0 gm (0.04 mole) of 1-(2-hydroxyethoxy)ethylpiperazine, and 3.2 gm (0.08 mole) of sodium hydroxide. This reaction mixture was heated at gentle reflux for 20 hrs and the sample was analyzed by HPLC. The analysis revealed that starting material remains less than 1%. The reaction mixture was cooled to room temperature and treated with 70 cc 1N hydrochloric acid solution to get a pH in between 1 to 2. The layers were separated and the aqueous layer was diluted with 100 cc toluene and pH was adjusted to about 8 to 9 using sodium carbonate. The layers were separated and aqueous layer was extracted with 100 cc toluene. The organic layers were combined and washed with 2×100 cc of water. The solvent was distilled under vacuum at 70° C. to 80° C. to afford 12 gm oil. HPLC area %: 66.47%

Example-6

Preparation of 11-[4-[2-(2-Hydroxyethoxy)ethyl]-1-piperazinyl]dibenzo[b,f][1,4]thiazepine A 1 liter round bottom flask equipped with stirring rod, thermo pocket, reflux condenser and nitrogen inlet was charged with 10 gm (0.04 moles) of 11-chlorodibenzo[b,f][1, 4]-thiazepine, 100 cc toluene and the mixture was stirred for 15 min. at room temperature. The resulting solution was combined with 7.0 gm (0.04 mole) of 1-(2-hydroxyethoxy) ethylpiperazine, 9.7 gm (0.08 mole) of NN-dimethyl aniline. This reaction mixture was heated at gentle reflux for 40 hrs and the sample was analyzed by HPLC. The analysis revealed that starting material remains less than 1%. The reaction mixture was cooled to room temperature and treated with 175 cc 1N hydrochloric acid solution to get a pH in between 1 to 2. The layers were separated and the aqueous layer was diluted with 100 cc toluene and pH was adjusted to about 8 to 9 with sodium carbonate. The layers were separated and aqueous layer was extracted with 100 cc toluene. The organic layers were combined and washed with 2×100 cc of water. The solvent was distilled under vacuum at 70° C. to 80° C. to afford 12 gm oil. HPLC area %: 96.52

Example-7

Preparation of 11-[4-[2-(2-Hydroxyethoxy)ethyl]-1-piperazinyl]dibenzo[b,f][1,4]thiazepine A 1 liter round bottom flask equipped with stirring rod, thermo pocket, reflux condenser and nitrogen inlet was charged with 10 gm (0.04 moles) of 11-chlorodibenzo[b,f][1,4]-thiazepine, and 100 cc toluene and the mixture was stirred for 15 min. at room temperature. The resulting solution was combined with 7.0 gm (0.04 mole) of 1-(2-hydroxyethoxy) ethylpiperazine, 10.3 gm (0.08 mole) of N,N-diisopropyl ethyl aniline. This reaction mixture was heated at gentle reflux for 38 hrs and the sample was analyzed by HPLC. The analysis revealed that starting material remains less than 1%. The reaction mixture was cooled to room temperature and treated with 175 cc 1N hydrochloric acid solution to get a pH in between 1 to 2. The layers were separated and the aqueous layer was diluted with 100 cc toluene and pH was adjusted to about 8 to 9 with sodium carbonate. The layers were separated and aqueous layer was extracted with 100 cc toluene. The organic layers were combined and washed with 2×100 cc of water. The solvent was distilled under vacuum at 70° C. to 80° C. to afford 12 gm oil. HPLC area %: 90.64

Example-8

Preparation of 11-[4-[2-(2-Hydroxyethoxy)ethyl]-1-piperazinyl]dibenzo[b,f][1,4]thiazepine A 1 liter round bottom flask equipped with stirring rod, thermo pocket, reflux condenser and nitrogen inlet was charged with 10 gm (0.04 moles) of 11-chlorodibenzo[b,f][1,4]-thiazepine, 100 cc toluene and the mixture was stirred for 15 min. at room temperature. The resulting solution was combined with 7.0 gm (0.04 mole) of 1-(2-hydroxyethoxy) ethylpiperazine, 8.0 gm (0.08 mole) of triethyl amine. This reaction mixture was heated at gentle reflux for 35 hrs and the sample was analyzed by HPLC. The analysis revealed that starting material remains less than 1%. The reaction mixture was cooled to room temperature and treated with 175 cc 1N hydrochloric acid solution to get a pH in between 1 to 2. The layers were separated and the aqueous layer was combined with 100 cc toluene and pH was adjusted to about 8 to 9 by addition of sodium carbonate. The layers were separated and aqueous layer was extracted with 100 cc toluene. The organic layers were combined and washed with 2×100 cc of water. The solvent was distilled under vacuum at 70° C. to 80° C. to afford 15 gm oil. HPLC area %: 97.7

Example-9

Preparation of 11-[4-[2-(2-Hydroxyethoxy)ethyl]-1-piperazinyl]dibenzo[b,f][1,4]thiazepine A 1 liter round bottom flask equipped with stirring rod, thermo pocket, reflux condenser and nitrogen inlet was charged with 10 gm (0.04 moles) of 11-chlorodibenzo[b,f][1,4]-thiazepine, and 100 cc toluene and the mixture was stirred for 15 min. at room temperature. The resulting solution was treated with 7.0 gm (0.04 mole) of 1-(2-hydroxyethoxy)ethylpiperazine, 6.7 gm (0.08 mole) of sodium bicarbonate. This reaction mixture was heated at gentle reflux for 35 hrs and the sample was analyzed by HPLC. The analysis revealed that starting material remains less than 1%. The reaction mixture was cooled to room temperature and treated with 175 cc 1N hydrochloric acid solution to get a pH in between 1 to 2. The layers were separated and the aqueous layer was diluted with 100 cc toluene and pH was adjusted to about 8 to 9 with sodium carbonate. The layers were separated and the aqueous layer was extracted with 100 cc toluene. The organic layers were combined and washed with 2×100 cc of water. The solvent was distilled-off under vacuum at 70° C. to 80° C. to afford 14 gm oil. HPLC area %: 94.68

Example-10

Preparation of 11-[4-[2-(2-Hydroxyethoxy)ethyl]-1-piperazinyl]dibenzo[b,f][1,4]thiazepine A 1 liter round bottom flask equipped with stirring rod, thermo pocket, reflux condenser and nitrogen inlet was charged with 10 gm (0.04 moles) of 11-chlorodibenzo[b,f][1,4]-thiazepine, and 100 cc toluene and the mixture was stirred for 15 min. at room temperature. The resulting solution was combined with 7.0 gm (0.04 mole) of 1-(2-hydroxyethoxy) ethylpiperazine, 8.0 gm (0.08 mole) of potassium bicarbonate. This reaction mixture was heated at gentle reflux for 35 hrs and the sample was analyzed by HPLC. The analysis revealed that starting material remains less than 1%. The reaction mixture was cooled to room temperature and treated with 175 cc 1N hydrochloric acid solution to get a pH in between 1 to 2. The layers were separated and the aqueous layer was diluted with 100 cc toluene and pH was adjusted to about 8 to 9 with sodium carbonate. The layers were separated and aqueous layer was extracted with 100 cc toluene. The organic layers were combined and washed with 2×100 cc of water. The solvent was distilled-off under vacuum at 70° C. to 80° C. to afford 15 gm oil. HPLC area %: 98.54

Example 11

Preparation of 11-[4-[2-(2-Hydroxyethoxy)ethyl]-1-piperazinyl]dibenzo[b,f][1,4]thiazepine A 1 liter round bottom flask equipped with stirring rod, thermo pocket, reflux condenser and nitrogen inlet was charged with 10 gm (0.04 moles) of 11-chlorodibenzo[b,f][1,4]-thiazepine, 100 cc toluene and the mixture was stirred for 15 min. at room temperature. The resulting solution was combined with 7.7 gm (0.044 mole) of 1-(2-hydroxyethoxy) ethylpiperazine, 8.5 gm (0.08 mole) of sodium carbonate and 7.7 gm (0.026 mole) of tetra butyl ammonium bromide. This reaction mixture was heated at gentle reflux for 22 hrs and the sample was analyzed by HPLC. The analysis revealed that less than 1% of the starting material remained. The reaction mixture was cooled to room temperature and treated with 175 cc 1N hydrochloric acid solution to get a pH in between 1 to 2. The layers were separated and the aqueous layer was extracted with 100 cc toluene and pH was adjusted to about 8 to 9 with sodium carbonate. The layers were separated and aqueous layer was extracted with 100 cc toluene. The organic layers were combined and washed with 2×100 cc of water. The solvent was distilled under vacuum at 70° C. to 80° C. to afford 12 gm oil. HPLC area %: 98.87

Example-12

Preparation of 11-[4-[2-(2-Hydroxyethoxy)ethyl]-1-piperazinyl]dibenzo[b,f][1,4]thiazepine A 1 liter round bottom flask equipped with stirring rod, thermo pocket, reflux condenser and nitrogen inlet was charged with 10 gm (0.04 moles) of 11-chlorodibenzo[b,f][1,4]-thiazepine, 100 cc toluene and the mixture was stirred for 15 min. at room temperature. The resulting solution was combined with 7.7 gm (0.044 mole) of 1-(2-hydroxyethoxy) ethylpiperazine, 8.5 gm (0.08 mole) of sodium carbonate and 4.0 gm (0.02 mole) of trimethylsilyl iodide. This reaction mixture was heated at gentle reflux for 18 hrs and the sample was analyzed by HPLC. The analysis revealed that starting material remains less than 1%. The reaction mixture was cooled to room temperature and treated with 175 cc 1N hydrochloric acid solution to get a pH in between 1 to 2. The layers were separated and the aqueous layer was diluted with 100 cc toluene and pH was adjusted between 8 to 9 with sodium carbonate. The layers were separated and aqueous layer was extracted with 100 cc toluene. The organic layers were combined and washed with 2×100 cc of water. The solvent was distilled under vacuum at 70° C. to 80° C. to afford 0.9 gm oil. HPLC area %: 98.9

Example 13

Preparation of 11-[4-[2-(2-Hydroxyethoxy)ethyl]-1-piperazinyl]dibenzo[b,f][1,4]thiazepine fumarate A 2 liter round bottom flask equipped with stirring rod, thermo pocket, reflux condenser and nitrogen inlet was charged with 50 gm (0.2 moles) of 11-chlorodibenzo[b,f][1,4]-thiazepine (I), 500 cc toluene and the mixture was stirred for 15 min. at room temperature. The resulting solution was combined with 39 gm (0.22 mole) of 1-(2-hydroxyethoxy) ethylpiperazine (II), 56.2 gm (0.40 mole) of potassium carbonate and 16.89 gm (0.10 mole) of potassium iodide. The reaction mixture was heated at gentle reflux for 12 hrs and a sample of the reaction mixture was analyzed by HPLC. The analysis revealed that less than 1% of the starting material remained. The reaction mixture was cooled to room temperature and combined with 1000 cc 1N hydrochloric acid solution to get a pH in between 1 to 2. The layers were separated and the aqueous layer was diluted with 500 cc toluene and pH was adjusted to about 8 to 9 by addition of sodium carbonate. The layers (aqueous and nonaqueous reaction solvent toluene) were separated and the aqueous layer was extracted with 500 cc toluene. The organic (toluene) layers were combined and washed with 2×500 cc of water. The reaction solvent (toluene) was distilled-off under vacuum at 70 to 80° C., leaving 50 to 60 cc toluene. To this solution 950 to 1000 cc absolute ethanol was added with activated carbon 5 to 6 gm and heated to reflux for 90 min. The mixture was then cooled to 55 to 60° C. and filtered. The filtrate was further cooled to 25 to 30° C., and fumaric acid 8 to 9 gm was added with stirring. The mixture was heated to reflux for 120 min, cooled slowly to 25 to 30° C., maintained for 120 min, filtered, and washed with 175 to 200 cc absolute ethanol. The wet material obtained was dried under vacuum at 50 to 60° C. to produce quetiapine fumarate (50 to 55 gm).

Example 14

Preparation of 11-[4-[2-(2-Hydroxyethoxy)ethyl]-1piperazinyl]dibenzo[b,f][1,4]thiazepine fumarate A 2 liter round bottom flask equipped with stirring rod, thermo pocket, reflux condenser and nitrogen inlet was charged with 50 gm (0.2 moles) of 11-chlorodibenzo[b,f][1,4]-thiazepine (I) and 500 cc xylene and the mixture was stirred for 15 min. at room temperature. The resulting solution was combined with 39 gm (0.22 mole) of 1-(2-hydroxyethoxy)ethylpiperazine, 56.2 gm (0.40 mole) of potassium carbonate and 16.89 gm (0.10 mole) of potassium iodide. The reaction mixture was heated at gentle reflux for 12 hrs and a sample of the reaction mixture was analyzed by HPLC. The analysis revealed that less than 1% of starting material I remained. The reaction mixture was cooled to room temperature and treated with 1000 cc 1N hydrochloric acid solution to get a pH in between 1 to 2. The layers were separated and the aqueous layer was agitated with 500 cc xylene and the pH was adjusted to about 8 to 9 by addition of sodium carbonate. The layers were separated and the aqueous layer was extracted with 500 cc xylene. The organic (xylene reaction solvent) layers were combined and washed with 2×500 cc of water. The solvent was distilled-off under vacuum at 70 to 80° C., leaving 50 to 60 cc. toluene. To this solution 950 to 1000 cc absolute ethanol was added with activated carbon 5 to 6 gm and heated to reflux for 90 min. The mixture was cooled to 55 to 60° C. and filtered. The filtrate was further cooled to 25 to 30° C., and fumaric acid 8 to 9 gm was added with stirring. The mixture was heated to reflux for 120 min, cooled slowly to 25 to 30° C., maintained for 120 min, filtered, and washed with 175 to 200 cc. of absolute ethanol. The wet material obtained was dried under vacuum at 50 to 60° C. to produce quetiapine fumarate (50 to 55 gm).

Example 15

Preparation of 1-[4-[2-(2-Hydroxyethoxy)ethyl]-1-piperazinyl]dibenzo[b,f][1,4]thiazepine fumarate A 2 liter round bottom flask equipped with stirring rod, thermo pocket, reflux condenser and nitrogen inlet was charged with 50 gm (0.2 moles) of 11-chlorodibenzo[b,f][1,4]-thiazepine and 500 cc n-butanol and the mixture was stirred for 15 min. at room temperature. The resulting solution was combined with 39 gm (0.22 mole) of 1-(2-hydroxyethoxy)ethylpiperazine, 56.2 gm (0.40 mole) of potassium carbonate and 16.89 gm (0.10 mole) of potassium iodide. The reaction mixture was heated at gentle reflux for 12 hrs and a sample of the reaction mixture was analyzed by HPLC. The analysis revealed that starting material remains less than 1%. The reaction mixture was cooled to room temperature and treated with 1000 cc 1N hydrochloric acid solution to get a pH in between 1 to 2. The layers (aqueous and nonaqueous reaction solvent) were separated and the aqueous layer was extracted with 500 cc toluene and pH was adjusted to about 8 to 9 by addition of sodium carbonate. The layer s were separated and aqueous layer was again extracted with 500 cc toluene. The organic layers (n-butanol and toluene) were combined and washed with 2×500 cc of water. The solvent was distilled under vacuum at 70 to 80° C. to obtain an oil. To this oil 50 to 75 cc. toluene was added with 750 to 1000 cc absolute ethanol and activated carbon 5 to 6 gm, and heated to reflux for 90 min. The mixture was cooled to 55 to 60° C. and filtered. The filtrate was further cooled to 25 to 30° C. and fumaric acid 7 to 7.5 gm was added with stirring. The mixture was heated to reflux for 120 min, cooled slowly to 25 to 30° C., maintained for 120 min, filtered, and washed with 125 to 150 cc. of absolute ethanol. The wet material obtained was dried under vacuum at 50 to 60° C. to produce quetiapine fumarate (40 to 45 gm).

Example 16

Preparation of 11-[4-[2-(2-Hydroxyethoxy)ethyl]-1-piperazinyl]dibenzo[b,f][1,4]thiazepine fumarate A 1 liter round bottom flask equipped with stirring rod, thermo pocket, reflux condenser and nitrogen inlet was charged with 10 gm (0.04 moles) of 11-chlorodibenzo[b,f][1,4]-thiazepine, 100 cc toluene and the mixture was stirred for 15 min. at room temperature. The resulting solution was combined with 7.7 gm (0.044 mole) of 1-(2-hydroxyethoxy) ethylpiperazine, 8.5 gm (0.08 mole) of sodium carbonate and 1.6 gm (0.01 mole) of sodium iodide. This reaction mixture was heated at gentle reflux for 15 hrs and the sample was analyzed by HPLC. The analysis revealed that starting material remains less than 1%. The reaction mixture was cooled to room temperature and treated with 175 cc 1N hydrochloric acid solution to get a pH in between 1 to 2. The layers were separated and the aqueous layer was diluted with 100 cc toluene and pH was adjusted to about 8 to 9 with sodium carbonate. The layer s were separated and aqueous layer was extracted with 100 cc toluene. The organic layers were combined and washed with 2×100 cc of water. The solvent was distilled under vacuum at 70 to 80° C., leaving 10 to 15 cc toluene. To this solution 175 to 200 cc absolute ethanol was added with activated carbon 1 to 1.5 gm and heated to reflux for 90 min. The mixture was cooled to 55 to 60° C. and filtered. The filtrate was further cooled to 25 to 30° C., and fumaric acid 1.5 to 2.0 gm was added with stirring. The mixture was heated to reflux for 120 min, cooled slowly to 25 to 30° C., maintained for 120 min, filtered, and washed with 30 to 40 cc. of absolute ethanol. The wet material obtained was dried under vacuum at 50 to 60° C. to produce quetiapine fumarate (8 to 10 gm).

Example 17

Preparation of 11-[4-[2-(2-Hydroxyethoxy)ethyl]-1-piperazinyl]dibenzo[b,f][1,4]thiazepine A 1 liter round bottom flask equipped with stirring rod, thermo pocket, reflux condenser and nitrogen inlet was charged with 10 gm (0.04 moles) of 11-chlorodibenzo[b,f][1,4]-thiazepine (I), 100 cc toluene and the mixture was stirred for 15 min. at room temperature. The resulting solution was combined with 7.7 gm (0.044 mole) of 1-(2-hydroxyethoxy) ethylpiperazine (II), 8.5 gm (0.08 mole) of sodium carbonate carbonate and 7.7 gm (0.24 mole) of tetra butyl ammonium bromide. The reaction mixture was heated at gentle reflux for 22 hrs and a sample of the reaction mixture was analyzed by HPLC. The analysis revealed that less than 2% of the starting material remained. The reaction mixture was cooled to room temperature and combined with 300 cc 1N hydrochloric acid solution to get a pH in between 1 to 2. The layers were separated and the aqueous layer was diluted with 100 cc toluene and pH was adjusted between 8 to 9 by addition of sodium carbonate. The layers (aqueous and nonaqueous reaction solvent toluene) were separated and the aqueous layer was extracted with 100 cc toluene. The organic (toluene) layers were combined and washed with 2×100 cc of water. The reaction solvent (toluene) was distilled-off under vacuum at 70 to 80° C. to afford 12 gm oil. HPLC area %: 98.87

Example 18

Preparation of 11-[4-[2-(2-Hydroxyethoxy)ethyl]-1-piperazinyl]dibenzo[b,f][1,4]thiazepine A 2 liter round bottom flask equipped with stirring rod, thermo pocket, reflux condenser and nitrogen inlet was charged with 50 gm (0.2 moles) of 11-chlorodibenzo[b,f][1,4]-thiazepine (1), 500 cc toluene and the mixture was stirred for 15 min. at room temperature. The resulting solution was combined with 39 gm (0.22 mole) of 1-(2-hydroxyethoxy) ethylpiperazine (II), 56.2 gm (0.40 mole) of potassium carbonate and 16.89 gm (0.10 mole) of potassium iodide. The reaction mixture was heated at gentle reflux for 12 hrs and a sample of the reaction mixture was analyzed by HPLC. The analysis revealed that less than 1% of the starting material remained. The reaction mixture was cooled to room temperature and combined with 1000 cc 1N hydrochloric acid solution to get a pH in between 1 to 2. The layers were separated and the aqueous layer was diluted with 500 cc toluene and pH was adjusted between 8 to 9 by addition of sodium carbonate. The layers (aqueous and nonaqueous reaction solvent toluene) were separated and the aqueous layer was extracted with 500 cc toluene. The organic (toluene) layers were combined and washed with 2×500 cc of water. The reaction solvent (toluene) was distilled-off under vacuum at 70 to 80° C. to afford 60 gm oil. The above oil is crystallized using ethyl acetate to afford 11-[4-[2-(2-Hydroxyethoxy)ethyl]-1-piperazinyl]dibenzo[b,f][1,4]thiazepine 55 gm.

What claimed is:

1. A method for preparing quetiapine, 11-[4-[2-(2-hydroxyethoxy)ethyl]-1-piperazinyl]dibenzo[bf][1,4]thiazepine comprising the steps of: combining 11-chlorodibenzo[bf][1,4]thiazepine (I) with about 1 to about 1.5 molar equivalents with respect to (I) of 1-(2-hydroxyethoxy)ethyl piperazine (II),

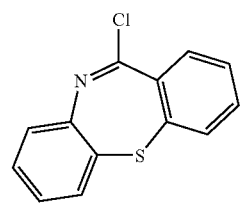

I

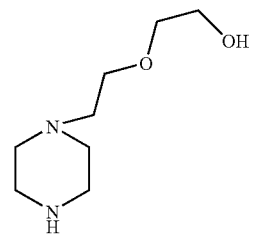

II a base, and phase transfer catalyst or a halide that is either an alkali metal halide or a silyihalide in a reaction solvent to obtain a reaction mixture, and heating the reaction mixture at a reaction temperature from about room temperature to reflux temperature for a reaction time.

2. The method of claim 1, wherein the molar amount of 1-(2-hydroxyethoxy)ethyl piperazine (II) is about 1 to about 1.2 molar equivalents with respect to 11-chlorodibenzo[bf][1,4]thiazepine (I).

3. The method of claim 1, wherein the reaction temperature is reflux temperature.

4. The method of claim 1, wherein the base is an organic base that is an amine.

5. The method of claim 4, wherein the amine is a tertiary amine.

6. The method of claim 1, wherein the base is an inorganic base that is an alkali metal carbonate, bicarbonate, or hydroxide.

7. The method of claim 6, wherein the inorganic base is selected from the group consisting of potassium bicarbonate, sodium bicarbonate, and sodium hydroxide.

8. The method of claim 6, wherein the base is an alkali metal carbonate that is potassium carbonate.

9. The method of claim 1, wherein the base is used in a molar amount between about 1 and about 3 molar equivalents with respect to the molar amount of 11-chlorodibenzo[bf][1,4]thiazepine (I) used in the reaction.

10. The method of claim 9, wherein the base is used in a molar amount of about 2 molar equivalents with respect to the molar amount of 11-chlorodibenzo[bf][1,4]thiazepine (I).

11. The method of claim 1, wherein the halide is an alkali metal fluoride, iodide, or bromide.

12. The method of claim 11, wherein the alkali metal halide is an alkali metal iodide.

13. The method of claim 12, wherein the alkali metal iodide is potassium iodide.

14. The method of claim 1, wherein the halide is used in a molar ratio of at least about 0.2 relative to the moles of 11-chlorodibenzo[bf][1,4]thiazepine (I) used.

15. The method of claim 1, wherein the reaction solvent is a nonhalogenated aromatic hydrocarbon, an alkyl ester, a mixture of a nonhalogenated aromatic hydrocarbon and an alkyl ester, or an alkyl alcohol.

16. The method of claim 15, wherein the reaction solvent is toluene or xylene or a mixture thereof.

17. The method of claim 15, wherein the reaction solvent is an alkyl alcohol or a mixture of alkyl alcohols.

18. The method of claim 1, wherein the reaction time is about 20 hours or less.

19. The method of claim 1, wherein the reaction time is about 10 to about 14 hours.

20. The method of claim 1, wherein the reaction time is monitored by the disappearance of compound I using thin layer chromatography, gas-liquid chromatography, or high pressure liquid chromatography.

21. The method of claim 1 further comprising the step of converting the quetiapine to a pharmaceutically acceptable salt.

22. The method of claim 21, wherein the pharmaceutically acceptable salt is quetiapine fumarate or quetiapine hemifumarate and wherein the conversion is effected by combining fumaric acid with the quetiapine.

23. The method of claim 21, wherein the quetiapine is combined with the fumaric acid in a solvent that is either the reaction solvent or a salification solvent.

24. The method of claim 23, wherein the combining is in the reaction solvent and the quetiapine is not isolated from said reaction solvent prior to combination with fumaric acid.

25. The method of claim 23, wherein the solvent is a salification solvent that is one or more aromatic hydrocarbons, or one or more $C_1$ to $C_4$ alcohol.

26. The method of claim 25, wherein the salification solvent is toluene or ethanol.

27. The method in claim 24 wherein, prior to combination with fumaric acid, the quetiapine in the reaction solvent is heated to about reflux temperature and subsequently cooled to about 30° C. to about 60° C., whereafter the fumaric acid is combined.

28. The method in claim 1, wherein the phase transfer catalyst is an ammonium salt selected from the group consisting of tricaprylylmethylammonium chloride, tetra-N-butylammonium bromide (TBAB), benzyltriethylammonium chloride (TEBA), cetyltrimethylammonium bromide, cetylpyridinium bromide, N-benzylquininium chloride, tetra-N-butylammonium chloride, tetra-N-butylammonium hydroxide, tetra-N-butylammonium iodide, tetraethylammonium chloride, benzyltributylammonium bromide, benzyltriethylammonium bromide, hexadecyltriethylammonium chloride, tetramethylammonium chloride, hexadecyltrimethyl ammonium chloride, and octyltrimethylammonium chloride.

29. The method in claim 28, wherein the phase transfer catalyst is selected from the group consisting of tricaprylylmethylammonium chloride, TBAB, TEBA and mixtures thereof.

* * * * *